United States Patent [19]

Ramey et al.

[11] 4,007,157

[45] Feb. 8, 1977

[54] SUBSTITUTED PIPERAZINES AND POLYMERIC COMPOSITIONS STABILIZED THEREBY

[75] Inventors: Chester E. Ramey, Spring Valley; John J. Luzzi, Carmel, both of N.Y.

[73] Assignee: Ciba-Geigy Corporation, Ardsley, N.Y.

[22] Filed: June 27, 1975

[21] Appl. No.: 591,222

Related U.S. Application Data

[63] Continuation of Ser. No. 378,368, July 11, 1973, abandoned, which is a continuation-in-part of Ser. No. 239,350, March 29, 1972, abandoned.

[52] U.S. Cl. .................... 260/45.8 N; 260/268 TR; 260/268 R
[51] Int. Cl.$^2$ ...................................... C07D 241/38
[58] Field of Search ............... 260/268 TR, 45.8 N

[56] References Cited

UNITED STATES PATENTS

| | | | |
|---|---|---|---|
| 3,318,876 | 5/1967 | Cignarella et al. | 260/268 C |
| 3,920,659 | 11/1975 | Ramey et al. | 260/268 TR |

*Primary Examiner*—Donald G. Daus
*Assistant Examiner*—Jose Tovar
*Attorney, Agent, or Firm*—Charles W. Vanecek

[57] ABSTRACT

Substituted piperazines are stabilizers for synthetic polymeric materials normally subject to deterioration caused by ultraviolet light. The compounds are prepared by the alkylation reaction between a substituted piperazine dione and an organic halide followed by reduction with lithium aluminum hydride. Polymeric compsitions containing these stabilizers may also contain a hindered phenolic compound. A typical embodiment is 15,15'-dodecamethylene-bis(7,15-diazadispiro[5,1,5,3]hexadecane).

23 Claims, No Drawings

SUBSTITUTED PIPERAZINES AND POLYMERIC COMPOSITIONS STABILIZED THEREBY

RELATED APPLICATIONS

This application is a continuation of application Ser. No. 378,368, filed July 11, 1973, now abandoned, which is a continuation-in-part of application Ser. No. 239,350, filed Mar. 29, 1972, now abandoned.

BACKGROUND OF THE INVENTION

This invention relates to the stabilization of organic material normally tending to deteriorate. In particular, the invention relates to the protection of synthetic polymers against the harmful degradative effects, such as discoloration and embrittlement caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirable physical properties when exposed to actinic light, while vinyl resins, such as polyvinyl chloride and polyvinyl acetate spot and degrade. The rate of air oxidation of polyolefins such as polyethylene and polypropylene is materially accelerated by ultraviolet light.

It has been proposed to stabilize polymeric materials against ultraviolet light deterioration by the use of various types of ultraviolet absorbers. Thus, U.S. Pat. No. 3,004,896 discloses for this purpose 2(2-hydroxyphenyl)benzotriazole derivatives, while U.S. Pat. No. 3,189,630 discloses certain metal salts of hydroxybenzoic acids which are useful as actinic stabilizers in synthetic polymers.

DETAILED DISCLOSURE

The present invention is directed to a class of ultraviolet light stabilizers which consist of a compound of the formula

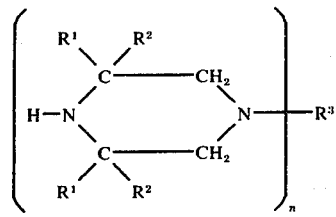

wherein
$R^1$ and $R^2$ are independently of each other methyl or ethyl or together with the carbon to which they are bound form a cyclopentyl or cyclohexyl ring, which is unsubstituted or substituted with a methyl group;
$n$ is an integer of from 1 to 2;
when $n$ is 1, $R^3$ is hydrogen, an alkyl group of from 1 to 20 carbon atoms or a benzyl group;
when $n$ is 2, $R^3$ is an alkylene group of from 1 to 20 carbon atoms.

By the term alkyl as represented by $R^1$ and $R^2$ is intended methyl or ethyl, with methyl being the preferred substituent. Representative of the cycloalkyl groups, as represented by $R^1$ and $R^2$, are cyclohexyl, cyclopentyl, 2-methyl, 3-methyl and 4-methylcyclohexyl, and 2-methyl and 3-methylcyclopentyl. The preferred cycloalkyl groups are cyclohexyl and 2-methylcyclohexyl.

This invention also relates to compositions of matter which are stabilized against ultraviolet light deterioration which comprises a synthetic organic polymer normally subject to ultraviolet deterioration containing from about 0.005 to 5% by weight of the polymer of the compounds of formula I and preferably from 0.01 to 2% by weight.

The piperazine derivatives as represented by formula I can be used in combination with other light stabilizers such as 2-(2-hydroxyphenyl)benzotriazoles, 2-hydroxybenzophenones, nickel complexes, and benzoates.

The stabilizers of this invention are suitable for the protection of many synthetic polymers from the deleterious effects of light. Homopolymers, copolymers, and mixtures thereof are embraced within the scope of substrates which may be stabilized with the stabilizers of this invention, along which may be mentioned, polystyrene and including homopolystyrene and copolymers with acrylonitrile and/or butadiene; vinyl resins formed from the polymerization of vinyl halides or from copolymerization of vinyl halides with unsaturated polymerizable compounds, for example, vinyl esters, $\alpha, \beta$-unsaturated acids, $\alpha, \beta$-unsaturated esters, and unsaturated hydrocarbons such as butadienes and styrene; poly-$\alpha$-olefins such as high and low density polyethylene, cross-linked polyethylene, polypropylene, poly(4-methyl-pentene-1), polybutene-1, and the like including copolymers of poly-$\alpha$-olefins such as ethylene-propylene copolymers, and the like; polybutadiene; polyisoprene; polyurethanes such as are prepared from polyols and organic polyisocyanate; polyamides such as hexamethylene-adipamide; polyesters such as polymethyleneterephthalates; polycarbonates such as those prepared from bisphenol-A and phosgene; polyacetals; polyethylene oxide; and polyacrylics such as polyacrylonitrile; polyphenyleneoxides such as those prepared from 2,6-dimethylphenol and the like. Particularly preferred polymers for the compositions of this invention are those normally solid polymers of alpha-olefins having up to 3 carbon atoms, e.g., ethylene, propylene and their copolymers.

The stabilized polymers of the present invention have utility in the normal uses for which plastics are employed and are particularly useful for film and fiber. Compounds of this invention may be incorporated in the polymeric substance during the usual processing operations, for example, by hot milling, the composition then being extruded, pressed, blow molded or the like into films, fibers, filaments, hollow spheres and the like. Where the polymer is prepared from a liquid monomer as in the case of styrene, the stabilizer may be dispersed or dissolved in the monomer prior to polymerization or curing.

In addition to the actinic stabilizers described, the plastic compositions may contain other additives such as plasticizers, pigments, fillers, dyes, glass or other fibers, thermal antioxidants, and the like. For example in most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005 to 5% and preferably from 0.01 to 2% by weight. Representative of such antioxidants are phosphite esters, such as triphenylphosphite and dibutylphosphite and alkyl arylphosphites such as dibutylphenylphosphite, and the like.

The best results are obtained with the preferred class of thermal antioxidants, the hindered phenols. These compounds have been found to provide the best thermal stabilization with the least discoloration in the compositions of the invention. Typical of these phenolic antioxidants include the following:

1. Phenolic compounds having the general formula

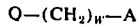

wherein
Q is

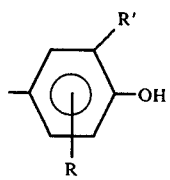

A is —CR(COOR")$_2$

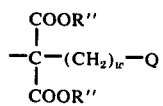

R is hydrogen or lower alkyl
R' is lower alkyl
R" is alkyl group having from 6–24 carbon atoms
W is an integer from 0 to 4.

Illustrative examples of the compounds shown above are
di-n-octadecyl α- (3,5-di-t-butyl-4-hydroxybenzyl)-malonate
di-n-octadecyl α-(3-t-butyl-4-hydroxy-5-methyl-benzyl)malonate which is disclosed in the Netherlands Pat. No. 6,711,199, Feb. 19, 1968
di-n-octadecyl-α,α'bis-(3-t-butyl-4-hydroxy-5-methylbenzyl)malonate which is disclosed in the Netherlands Pat. No. 6,803,498, Sept. 18, 1968.

2. Phenolic compounds having the general formula

Q—R

Illustrative examples of the compounds shown above are
2,6-di-t-butyl-p-cresol
2-methyl-4,6-di-t-butylphenol and the like.

3. Phenolic compounds having the formula

2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-methylene-bis[6-(1-methylcyclohexyl)-4-methylphenol]
and the like.

4. Phenolic compounds having the formula

Illustrative examples of such compounds are
2,5-di-t-butylhydroquinone
2,6-di-t-butylhydroquinone
2,5-di-t-butyl-4-hydroxyanisole 5. Phenolic compounds having the formula

Illustrative examples of such compounds are
4,4'-thiobis-(2-t-butyl-5-methylphenol)
4,4'-thiobis-(2-t-butyl-6-methylphenol)
2,2'-thiobis-(6-t-butyl-4-methylphenol)

6. Phenolic compounds having the formula

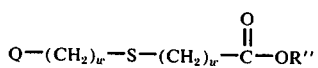

Illustrative examples of such compounds are
octadecyl-(3,5-dimethyl-4-hydroxybenzylthio)-acetate
dodecyl-(3,5-di-t-butyl-4-hydroxybenzylthio)-propionate 7. Phenolic compounds having the formula

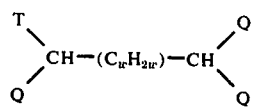

wherein
T is hydrogen
R or Q as defined above.

Illustrative examples of such compounds are
1,1,3-tris-(3,5-dimethyl-4-hydroxyphenyl)-propane
1,1,3-tris(5-t-butyl-4-hydroxy-2-methylphenyl)-butane
1,1,5,5-tetrakis-(3'-t-butyl-4'-hydroxy-6'-methylphenyl)-n-pentane 8. Phenolic compounds having the formula

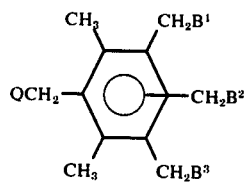

wherein B$^1$, B$^2$ and B$^3$ are hydrogen, methyl or Q, provided that when B$^1$ and B$^3$ are Q then B$^2$ is hydrogen or methyl and when B$^2$ is Q then B$^1$ and B$^3$ are hydrogen or methyl.

Illustrative examples of such compounds are
1,4-di(3,5-di-t-butyl-4-hydroxybenzyl)-2,3,5,6-tetramethylbenzene
1,3,5-tri(3,5-di-t-butyl-4-hydroxybenzyl)-2,4,6-trimethylbenzene 9. Phenolic compounds having the formula

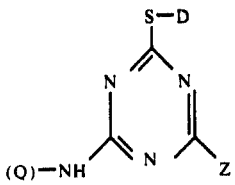

wherein

Z is NHQ, —S—D or —O—Q

D is alkyl group having from 6–12 carbon atoms or —(C$_W$H$_{2W}$)—S—R''

Illustrative examples of such compounds are 2,4-bis-(n-octylthio)-6-(3,5-di-t-butyl-4-hydroxyaniline)-1,3,5-triazine 6-(4-hydroxy-3-methyl-5-t-butylanilino)-2,4-bis-(n-octylthio)-1,3,5-triazine 6-(4-hydroxy-3,5-dimethylanilino)-2,4-bis-(n-octylthio)-1,3,5-triazine 6-(4-hydroxy-3,5-di-t-butylanilino)-2,4-bis-(n-octylthioethylthio)-1,3,5-triazine 6-(4-hydroxy-3,5-di-t-butylanilino)-4-(4-hydroxy-3,5-di-t-butylphenoxy)-2-(n-octylthio)-1,3,5-triazine 2,4-bis(4-hydroxy-3,5-di-t-butylanilino)-6-(n-octylthio)-1,3,5-triazine.

The above phenolic triazine stabilizers are more fully described in U.S. Pat. No. 3,255,191.

10. Phenolic compounds having the formula

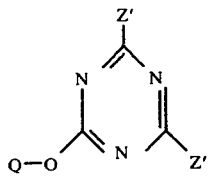

wherein Z' is —O—Q, —S—D or —S—(C$_W$H$_{2W}$)—SD

Illustrative examples of such compounds are 2,3-bis-(3,5-di-t-butyl-4-hydroxyphenoxy)-6-(n-octylthio)-1,3,5-triazine 2,4,6-tris-(4-hydroxy-3,5-di-t-butylphenoxy)-1,3,5-triazine.

6-(4-hydroxy-3,5-di-t-butylphenoxy)-2,4-bis-(n-octylthioethylthio)-1,3,5-triazine 6-(4-hydroxy-3-methylphenoxy)-2,4-bis-(n-octylthio)-1,3,5-triazine 6-(4-hydroxy-3-t-butylphenoxy)-2,4-bis-(n-octylthioethylthio)-1,3,5-triazine 6-(4-hydroxy-3-methyl-5-t-butylphenoxy)-2,4-bis-(n-octylthio)-1,3,5-triazine 2,4-bis-(4-hydroxy-3-methyl-5-t-butylphenoxy)-6-(n-octylthio)-1,3,5-triazine 2,4,6-tris-(4-hydroxy-3-methyl-5-t-butylphenoxy)-1,3,5-triazine 6-(4-hydroxy-3,5-di-t-butylphenoxy)-2,4-bis-(n-octylthiopropylthio)-1,3,5-triazine 6-(4-hydroxy-3,5-di-t-butylphenoxy)-2,4-bis(n-dodecylthioethylthio)-1,3,5-triazine 2,4-bis-(4-hydroxy-3,5-di-t-butylphenoxy)-6-butylthio-1,3,5-triazine 2,4-bis-(4-hydroxy-3,5-di-t-butylphenoxy)-6-(n-octadecylthio)-1,3,5-triazine 2,4-bis-(4-hydroxy-3,5-di-t-butylphenoxy)-6-(n-dodecylthio)-1,3,5-triazine 2,4-bis(4-hydroxy-3,5-di-t-butylphenoxy)-6-(n-octylthiopropylthio)-1,3,5-triazine 2,4-bis-(4-hydroxy-3,5-di-t-butylphenoxy)-6-(n-octylthioethylthio)-1,3,5-triazine 2,4-bis-(4-hydroxy-3,5-di-t-butylphenoxy)-6-(n-dodecylthioethylthio)-1,3,5-triazine.

The above phenolic triazine stabilizers are more fully described in U.S. Pat. No. 3,255,191.

11. Phenolic compounds having the formula $$[Q-C_xH_{2x}-COO-C_xH_{2x}]_pR'''-(R)_{4-p}$$

wherein p is an integer from 2 to 4 and

R''' is a tetravalent radical selected from
aliphatic hydrocarbons having from 1 to 30 carbon atoms
aliphatic mono and dithioethers having from 1 to 30 carbon atoms
aliphatic mono and diethers having from 1 to 30 carbon atoms and z is an integer from 0 to 6.

Illustrative examples of such compounds are

Sub-class I n-Octadecyl 3-(3,5-di-t-butyl-4-hydroxyphenyl)-propionate n-Octadecyl 2-(3,5-di-t-butyl-4-hydroxyphenyl)-acetate n-Octadecyl 3,5-di-t-butyl-4-hydroxybenzoate n-Hexyl 3,5-di-t-butyl-4-hydroxyphenylbenzoate n-Dodecyl 3,5-di-t-butyl-4-hydroxyphenylbenzoate Neo-dodecyl 3-(3,5-di-t-butyl-4-hydroxyphenyl)-propionate Dodecyl β-(3,5-di-t-butyl-4-hydroxyphenyl)-propionate Ethyl α-(4-hydroxy-3,5-di-t-butylphenyl)-isobutyrate Octadecyl α-(4-hydroxy-3,5-di-t-butylphenyl)-isobutyrate Octadecyl α-(4-hydroxy-3,5-di-t-butylphenyl)-propionate

Sub-class II 2-(n-octylthio)ethyl 3,5-di-t-butyl-4-hydroxybenzoate 2-(n-octylthio)ethyl 3,5-di-t-butyl-4-hydroxyphenylacetate 2-(n-octadecylthio)ethyl 3,5-di-t-butyl-4-hydroxyphenylacetate 2-(n-octadecylthio)ethyl 3,5-di-t-butyl-4-hydroxybenzoate 2-(2-hydroxyethylthio)ethyl 3,5-di-t-butyl-4-hydroxybenzoate 2,2'-Thiodiethanol bis(3,5-di-t-butyl-4-hydroxyphenyl)acetate Diethyl glycol bis-[3,5-di-t-butyl-4-hydroxyphenyl)-propionate]

2-(n-octadecylthio)ethyl 3-(3,5-di-t-butyl-4-hydroxyphenyl)propionate 2,2'-Thiodiethanol-bis-3-(3,5-di-t-butyl-4-hydroxyphenyl)propionate Stearamido N,N-bis-[ethylene 3-(3,5-di-t-butyl-4-hydroxyphenyl)propionate]

n-Butylimino N,N-bis-[ethylene 3-(3,5-di-t-butyl-4-hydroxyphenyl)propionate]

2-(2-stearoyloxyethylthio)ethyl 3,5-di-t-butyl-4-hydroxybenzoate 2-(2-hydroxyethylthio)ethyl 7-(3-methyl-5-t-butyl-4-hydroxyphenyl)heptanoate 2-(2-stearoyloxyethylthio)ethyl 7-(3-methyl-5-t-butyl-4-hydroxyphenyl)heptanoate

Sub-class III 1,2-propylene glycol bis-[3-(3,5-di-t-butyl-4-hydroxyphenyl)propionate]

Ethylene glycol bis-[3-(3,5-di-t-butyl-4-hydroxyphenyl) propionate]

Neopentylglycol bis-[3-(3,5-di-t-butyl-4-hydroxyphenyl)propionate]

Ethylene glycol bis-(3,5-di-t-butyl-4-hydroxyphenylacetate)

Glycerine-1-n-octadecanoate-2,3-bis(3,5-di-t-butyl-4-hydroxyphenylacetate

Pentaethylthritol-tetrakis-[3-(3',5'-di-t-butyl-4'-hydroxyphenyl)propionate]

1,1,1-trimethylol ethane-tris-3-(3,5-di-t-butyl-4-hydroxyphenyl)propionate

Sorbitol hexa-[3-(3,5-di-t-butyl-4-hydroxyphenyl)-propionate]

1,2,3-butanetriol tris-[3-(3,5-di-t-blutyl-4-hyroxyphenyl)propionate]

2-hydroxyethyl 7-(3-methyl-5-t-butyl-4-hydroxyphenyl)heptanoate 2-stearoyloxyethyl 7-(3-methyl-5-t-butyl-4-hydroxyphenyl)heptanoate 1,6-n-hexanediol-bis[(3',5'-di-t-butyl-4-hydroxyphenyl)propionate]

The above phenolic ester stabilizers of sub-classes I, II and III are more fully described in U.S. Pat. No. 3,330,859, and U.S. Pat. No. 3,644,482, respectively.

12. Phenolic compounds having the formula

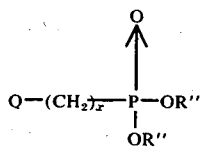

where
x is an integer of 1 to 2.

Illustrative examples of such compounds are

Di-n-octadecyl 3,5-di-t-butyl-4-hydroxybenzylphosphonate

Di-n-octadecyl 3-t-butyl-4-hydroxy-5-methylbenzylphosphonate

Di-n-octadecyl 1-(3,5-di-t-butyl-4-hydroxyphenyl)-ethanephosphonate

Di-n-tetradecyl 3,5-di-t-butyl-4-hydroxybenzylphosphonate

Di-n-hexadecyl 3,5-di-t-butyl-4-hydroxybenzylphosphonate

Di-n-docosyl-3,5-di-t-butyl-4-hydroxybenzylphosphonate

Di-n-octadecyl-3,5-di-t-butyl-4-hydroxybenzylphosphonate

The above di-(higher)alkyl phenolic phosphonates are more fully described in U.S. Pat. No. 3,281,505.

13. Phenolic compounds having the formula

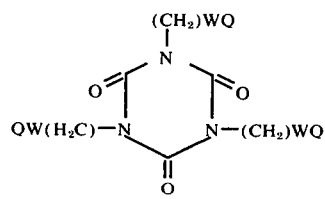

wherein W and Q are as defined above.

Illustrative examples of such compounds are
tris-(3,5-di-t-butyl-4-hydroxybenzyl)isocyanurate
tris-(3-t-butyl-4-hydroxy-5-methylbenzyl)isocyanurate The above hydroxyphenylalkenyl isocyanurates are more fully described in U.S. Pat. No. 3,531,483.

The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

The compounds of this invention when $R^3$ is other than hydrogen, may be prepared by reacting a substituted piperazine dione of the formula

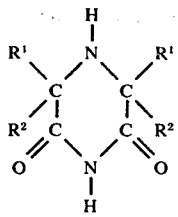

wherein $R^1$ and $R^2$, are as defined above with an organic mono or dihalo compound followed by reduction with lithium aluminum hydride. The alkylation reaction is carried out by first preparing the alkali or alkaline earth metal salt of the compound of formula II and reacting the resulting salt with the appropriate organic halide in a solvent such as dimethylformamide, isopropanol, or acetone at about 75° C. The compounds of this invention wherein $R^3$ is hydrogen are prepared by reducing the compounds of formula II with lithium aluminum hydride.

Compounds of formula II, wherein $R^1$ and $R^2$ form a mono cyclic ring with the carbon to which they are attached, may be prepared by the self condensation of a cycloalkyl amino cyanohydrin according to the procedure described by R. Sudo and S. Ichihera, Bull. Chem. Soc. Japan 36 34 (1963) and subsequent hydrolysis as described by E. F. J. Duynstee et al., Recueil de Chemie des Pays-Bas 87 945 (1968). The cycloalkylamino cyanohydrin is formed by the sequential addition of hydrogen cyanide and ammonia to a cycloalkanone as described by W. E. Noland, R. J. Sundberg and M. L. Michaelson, J. Org. Chem. 28 3576 (1963). Although the above references deal specifically with the cycloalkyl case, the procedures therein have been found to be operable in the alkyl case as well, for example substitution of an alkanone such as acetone for the cycloalkanone such as cyclohexanone in the above procedure.

Examples of organic halides which can be reacted with the salts of the compounds of formula II include organic monohalides such as methyliodide, ethyl chloride, propyl bromide, isopropyl chloride, butyl bromide, pentyl bromide, isopentyl chloride, hexyl bromide, octyl bromide, dodecyl bromide, tetradecyl chloride, hexadecyl bromide, octadecyl bromide, eicosyl bromide, benzyl chloride and the like; organic dihalides such as methylene bromide, dibromoethane, 1,3-dibromopropane, 1,3-dibromobutane, 1,4-dibromobutane, 1,8-dibromooctane, 1,12-dichlorododecane, 1,2-dichlorooctane, 1,18-dibromooctadecane, 1,20-dibromoeicosane, and the like. The preferred organic monohalide is an alkyl halide containing from 1 to 20 carbon atoms and the most preferred is an alkyl halide containing from 6 to 18 carbon atoms. The preferred dihalide contains from 2 to 12 carbons.

The preparation of the substituted piperazine diones of formula II and said alkylated compounds prepared therefrom are more fully disclosed in copending application filed on Mar. 24, 1972.

Another embodiment of this invention includes compounds of the formula

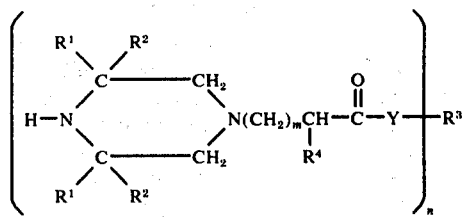

III wherein
R¹, R², R³ and n are as defined previously;
R⁴ is hydrogen or methyl;
Y is O or N; and
m is 0 or 1.

The compound of formula III when m is 1 may be prepared by reacting a compound of the formula

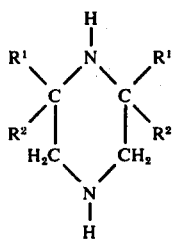

IV wherein R¹ and R² are as defined previously with an acrylate or acrylamide of the formula

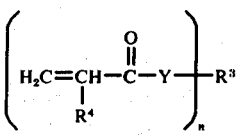

wherein R³, R⁴, Y and n are as defined previously. The reaction is carried out under a nitrogen atmosphere in a solvent such as toluene, at a temperature of about 90° C.

when m is 0, compounds of formula III are prepared by reacting compounds of formula IV with haloesters and haloamides of the formula

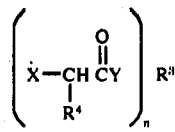

where X is a halogen such as chlorine or bromine.

The following examples, presented for illustration and not limitation, will further serve to typify the nature of the present invention.

EXAMPLE 1

7,15-diazadispiro[5,1,5,3]hexadecane

In a dry 2-liter Morton flask equipped with a stirrer, condenser, dropping funnel and N₂ inlet was placed a suspension of 6.43 g. of lithium aluminum hydride in 380 ml. of dry ether. To the suspension was added with stirring under an N₂ atmosphere a slurry of 17.6 g. (0.070 moles) of 7,15-diazadispiro[5,1,5,3] hexadecane-14,16-dione in 700 ml of ether at such a rate as to maintain gentle reflux. The reaction mixture was allowed to stir for 0.5 hours then heated to boiling under reflux for 21 hours. At the end of this time, the reaction mixture was cooled to 5° C and water was added carefully dropwise until the precipitated solids became white and granular. The solid precipitate was made filterable by the addition of 400 g. of anhydrous sodium sulfate. The reaction mixture was then filtered with suction and then collected solids were washed well with additional ether. The filtrate and ether washes were combined dried over anhydrous sodium sulfate and evaporated under reduced pressure. The residue was taken up in a minimum amount of a hot benzene and n-hexane was added at the boil until a precipitate formed. The solution was allowed to stand at room temperature about 48 hours followed by filtration to separate a minor amount of solids which formed. The filtrate was cooled to 5° C for about 14 hours and crystals formed were collected by suction yielding the product as white crystals, m.p. 89°–90° C.

In a similar manner, 1,9-dimethyl-7,15-diazadispiro[5,1,5,3]hexadecane is prepared by substituting for 7,15-diazadispiro[5,1,5,3]hexadecane-14,16-dione an equivalent amount of 1,9-dimethyl-7,15-diazadispiro[5,1,5,3]hexadecane-14,16-dione.

EXAMPLE 2

15-octadecyl-7,15-diazadispiro[5,1,5,3]hexadecane

In a dry 300 ml 3-necked flask equipped with a condenser with drying tube, thermometer, dropping funnel and a nitrogen inlet was placed 50 ml of ether and 0.82 g. (0.022 moles) of lithium aluminum hydride was added portionwise under a nitrogen atmosphere. The ether-LiAlH₄ slurry was cooled in an ice-bath and a solution of 4.5 g (0.009 moles) of 15-octadecyl-7,15-diazadispiro[5,1,5,3]hexadecane-14,16-dione in 100 ml of ether was added dropwise with stirring over a 1½ hour period. The reaction mixture was then heated to boiling under reflux for about 12 hours. The reaction mixture was cooled to 5° C and water was added dropwise carefully until the solids became white and granular. Anhydrous sodium sulfate was added to make the solids filterable. The reaction mixture was filtered with suction, the collected salts washed well with ether, and the ether filtrate and washings were combined and concentrated to dryness under reduced pressure. Recrystallization of the residue from acetone gave colorless crystals, m.p. 38°–41° C of the desired material.

The following the above procedure, and substituting for 15-n-octadecyl 7,15-diazadispiro[5,1,5,3]hexadeca-14,16-dione an equivalent amount of:
a. 15-benzyl-7,15-diazadispiro[5,1,5,3]hexadecane-14,16-dione
b. 15,15'-dodecanemethylene bis(7,15-diazadispiro[5,1,5,]hexadecane-14,16-dione)
c. 15,15'-n-octamethylene bis(7,15-diazadispiro[5,1,5,3]hexadecane-14,16-dione)
d. 15,15'-tetramethylene bis(7,15-diazadispiro[5,1,5,3]hexadecane-14,16-dione)
e. 15-methyl-7,15-diazadispiro[5,1,5,3]hexadecane-14,16-dione
f. 15-n-octyl-7,15-diazadispiro[5,1,5,3]hexadecane-14,16-dione
g. 4-n-octadecyl-2,2,6,6-tetramethyl-3,5-diketopiperazine
h. 4-benzyl-2,2,6,6-tetramethyl-3,5-diketopiperazine
i. 4,4'-(n-dodecanemethylene)bis(2,2,6,6-tetramethyl-3,5-diketopiperazine
j. 4,4'-(n-octamethylene)bis(2,2,6,6-tetramethyl-3,5-diketopiperazine
k. 4,4'(tetramethylene)bis(2,2,6,6-tetramethyl-3,5-diketopiperazine
l. 4-methyl-2,2,6,6-tetramethyl-3,5-diketopiperazine
m. 4-n-octyl-2,2,6,6-tetramethyl-3,5-diketopiperazine
n. 15-n-octadecyl-1,9-dimethyl-7,15-diazadispiro[5,1,5,3]hexadecane-14,16-dione there is respectively obtained the following compounds:
a. 15-benzyl-7,15-diazadispiro[5,1,5,3]hexadecane
b. 15,15'-dodecamethylene bis(7,15-diazadispiro[5,1,5,3]hexadecane) m.p. 102°–106° C
c. 15,15'-n-octamethylene bis(7,15-diazadispiro[5,1,5,3]hexadecane)
d. 15,15'-tetramethylene bis(7,15-diazadispiro[5,1,5,3]hexadecane)
e. 15-methyl-7,15-diazadispiro[5,1,5,3]hexadecane
f. 15-n-octyl-7,15-diazadispiro[5,1,5,3]hexadecane
g. 4-n-octadecyl-2,2,6,6-tetramethylpiperazine
h. 4-benzyl-2,2,6,6-tetramethylpiperazine
i. 4,4'(n-dodecamethylene)bis2,2,6,6-tetramethylpiperazine)
j. 4,4'(n-octamethylene)bis(2,2,6,6-tetramethylpiperazine
k. 4,4'(tetramethylene)bis(2,2,6,6-tetramethylpiperazine
l. 4-methyl-2,2,6,6-tetramethylpiperazine
m. 4-n-octyl-2,2,6,6-tetramethylpiperazine
n. 15-n-octadecyl-1,9-dimethyl-7,15-diazadispiro[5,1,5,3]hexadecane.

EXAMPLE 3

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The test conducted on polymers using an artificial light exposure device is described below:

a. Sample Preparation 5 mil Film — Unstabilized polypropylene powder (Hercules Profax 6501) is thoroughly blended with the indicated amounts of additives. The blended material is then milled on a two roll mill for 5 minutes at 182° C. The milled sheet is then compression molded at 220° C into 5 mil thick film under a pressure of 175 psi and water cooled in the press.

b. Testing Method

This test is conducted in a FS/BL unit, basically of the American Cyanamid design, which consists of 40 tubes of alternating fluorescent sun lamps and black lights (20 of each). The 5 mil sample film are mounted on 3 × 2" IR card holders with ¼" × 1" windows and are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

The test results reported below were obtained according to the procedures described above. The amounts of the additivies are expressed in weight percent based on the weight of the polymer.

Table I

| Formulation* | Time in Hours to .5 Carbonyl Absorbance Units |
|---|---|
| .5% 7,15-diazadispiro[5,1,5,3]hexadecane | 1490 |
| .5% 15-octadecyl-7,15-diazadispiro[5,1,5,3]hexadecane | 980 |
| .5% 15,15'-dodecamethylene bis (7,15-diazadispiro[5,1,5,3]hexadecane) | 1060 |
| Control* | 278 |

*Each of the samples tested and the control contains 0.2% of (di-n-octadecyl(3,5-di-t-butyl-4-hydroxybenzyl) phosphonate which is an antioxidant which prevents oxidative degradation of polypropylene.

Other hindered phenolic antioxidants may be used in place of di-octadecyl(3,5-di-t-butyl-4-hydroxybenzyl)-phosphonate in the above mentioned compositions for example, di-n-octadecyl α-(3-t-butyl-4-hydroxy-5-methylbenzyl)malonate, 2,4-bis-(n-octylthio)-6-(3,5-di-t-butyl-4-hydroxyaniline)-1,3,5-triazine, octadecyl 3-(3',5'-di-t-butyl-4'-hydroxyphenyl)propionate, pentaethylthritol-tetrakis[3-(3,5-di-t-butyl-4-hydroxyphenyl)propionate], tris-(3,5-di-t-butyl-4-hydroxybenzyl)isocyanurate respectively.

EXAMPLE 4 a. A composition comprising acrylonitrilebutadiene-styrene terpolymer and 1% by weight of 15,15'-n-dodecamethylene bis(7,15-diazadispiro[5,1,5,3]hexadecane) resists embrittlement due to exposure to ultraviolet light longer than one which does not contain the stabilizer.

b. A composition comprising a polyurethane prepared from toluene diisocyanate and alkylene polyols and 1.0% by weight of 15-benzyl-7,15-diazadispiro[5,1,5,3]hexadecane is more stable to sunlight, fluorescent sunlamps, black lights and fluorescent lights than the unformulated polyurethane.

c. A composition comprising a polycarbonate prepared from bisphenol-A and phosgene and 1% by weight of 4-n-octadecyl-2,2,6,6-tetramethylpiperazine resists discoloration due to exposure to ultraviolet light longer than one which does not contain the stabilizer.

d. A composition comprising a polyester (polyethyleneterephthalate) and 0.2% by weight of 7,15-diazadispiro[5,1,5,3]hexadecane resists discoloration due to exposure to ultraviolet light longer than one which does not contain the stabilizer.

e. A composition comprising polymethylmethacrylate and 0.25% by weight of 15,15'-n-dodecanemethylene bis(7,15-diazadispiro[5,1,5,3]hexadecane) resists discoloration due to exposure to ultraviolet light longer than one which does not contain the stabilizer.

EXAMPLE 5 a. A stabilized linear polyethylene is prepared by incorporating therein 0.5% by weight of 4-benzyl-2,2,6,6-tetramethylpiperazine. The stabilized compositions resist embrittlement due to exposure to ultraviolet light longer than one which does not contain the stabilizer.

b. A stabilized polyamide (nylon 6,6) is prepared by incorporating therein 0.1% of 15-n-octyadecyl-7,15-diazadispiro[5,1,5,3]hexadecane. The light stability of the stabilized composition is superior to that of an unstabilized polyamide.

c. A stabilized polyphenylene oxide polymer (prepared by polymerizing 2,6-dimethylphenol) is prepared by incorporating therein 0.5% by weight 15,15'-tetramethylene bis(7,15-diazadispiro[5,1,5,3]hexadecane). The stabilized compositions resist embrittlement due to exposure to ultraviolet light longer than one which does not contain the stabilizer.

d. A stabilized crystalline polystyrene is prepared by incorporating therein 0.1% by weight of 4,4'-(dodecamethylene)bis(2,2,6,6-tetramethylpiperazine). The stabilized compositions resist embrittlement due to exposure to ultraviolet light longer than one which does not contain the stabilizer.

EXAMPLE 6

High impact polystyrene resin containing elastomer (i.e., butadiene-styrene) is stabilized against loss of elongation properties due to exposure to ultraviolet light by incorporation of 0.3% by weight of 15-n-octadecyl-7,15-diazadispiro[5,1,5,3]hexadecane The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C and a pressure of 2,000 pounds per square inch into a sheet of uniform thickness (25 mil). The sheets are then cut into strips approximately 4 × 0.5 inches. A portion of these strips is then measured for percent of elongation in the Instron Tensile Testing Apparatus (Instron Engineering Corporation, Quincy, Massachusetts). The remaining portion of the strips are placed in an FS/BL chamber according to Example 6 (b) except that the time to 50% reduction in elongation is measured. The stabilized polystyrene resin retains its elongation property longer than the unstabilized resin.

Similar results are obtained when an equivalent amount of the following stabilizers are used in place of the above mentioned stabilizer.

a. 0.1% by weight of 4,4'(tetramethylene) bis(2,2,6,6-tetramethylpiperazine)

b. 0.2% by weight of 15,15'-n-octamethylene bis(7,15-diazadispiro[5,1,5,3]hexadecane)

c. 1.0% by weight of 15-methyl-7,15-diazadispiro[5,1,5,3]hexadecane d. 0.1% by weight of 4-n-octadecyl-2,2,6,6-tetramethylpiperazine e. 0.1% by weight of 4-methyl-2,2,6,6-tetramethylpiperazine f. 0.5% by weight of 4,4'(n-octamethylene) bis(2,2,6,6-tetramethylpiperazine)

g. 1% by weight of 4-n-octyl-2,2,6,6-tetramethylpiperazine h. 0.5% by weight of 15-n-octadecyl-1,9-dimethyl-7,15-diazadispiro[5,1,5,3]hexadecane.

Antioxidants may also be incorporated into each of the above mentioned compositions for example, di-n-octadecyl-α,α'-bis(3-t-butyl-4-hydroxy-5-methylbenzyl) malonate, 2,4-bis(4-hydroxy-3,5-di-t-butylphenoxy)-6-(n-octylthioethylthio)-1,3,5-triazine, 2,4-bis(3,5-di-t-butyl-hydroxyphenoxy)-6-(n-octylthio)-1,3,5-triazine di-n-octadecyl 3,5-di-t-butyl-4-hydroxybenzyl phosphonates and octadecyl 3(3',5'-di-t-butyl-4-hydroxyphenyl)propionate respectively.

What is claimed is:

1. A compound of the formula

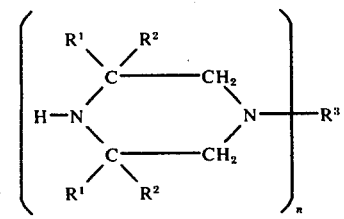

wherein

R¹ and R² together with the carbon to which they are bound form a cyclopentyl or cyclohexyl ring, which is unsubstituted or substituted with a methyl group;

$n$ is an integer of from 1 to 2;

when $n$ is 1, R³ is hydrogen, alkyl of from 1 to 20 carbon atoms or benzyl;

when $n$ is 2, R³ is alkylene of from 1 to 20 carbon atoms.

2. A compound of the formula

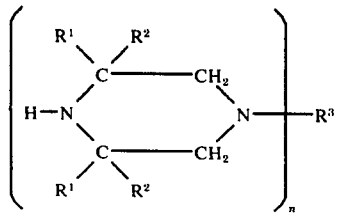

wherein $R^1$ and $R^2$ together with the carbon to which they are bound form a cyclopentyl or cyclohexyl ring, which is unsubstituted or substituted with a methyl group;

$n$ is an integer of from 1 to 2;

when $n$ is 1, $R^3$ is hydrogen or alkyl of from 1 to 20 carbon atoms;

when $n$ is 2, $R^3$ is alkylene of from 1 to 20 carbon atoms.

3. A compound according to claim 2 having the formula

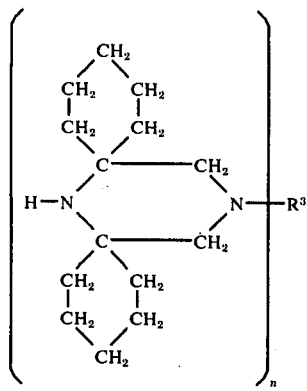

wherein $n$ is an integer of from 1 to 2;

when $n$ is 1, $R^3$ is hydrogen, alkyl of from 1 to 20 carbon atoms;

when $n$ is 2, $R^3$ is alkylene of from 1 to 20 carbon atoms.

4. A compound according to claim 3 wherein
$n$ is 1;
$R^3$ is hydrogen or alkyl having from 6 to 18 carbon atoms.

5. A compound according to claim 3 wherein
$n$ is 2;
$R^3$ is alkylene having from 2 to 12 carbon atoms.

6. A compound according to claim 2 which is 7,15-diazadispirol[5,1,5,3]hexadecane.

7. A compound according to claim 2 which is 15-n-octadecyl-7,15-diazadispiro[5,1,5,3]hexadecane.

8. A compound according to claim 2 which is 15-n-octadecyl-1,9-dimethyll-7,15-diazadispiro[5,1,5,3] hexadecane.

9. A compound according to claim 1 which is 15-benzyl-7,15-diazadispiro[5,1,5,3]hexadecane.

10. A compound according to claim 2 which is 15,15'-dodecamethylene bis(7,15-diazadispiro[5,1,5,3] hexadecane).

11. A compound according to claim 2 which is 15,15'-octamethylene bis(7,15-diazadispiro[5,1,5,3] hexadecane).

12. A compound according to claim 2 which is 15,15':tetramethylene bis(7,15-diazadispiro[5,1,5,3] hexadecane).

13. A compound according to claim 2 which is 15-methyl-7,15-diazadispiro[5,1,5,3]hexadecane.

14. A compound according to claim 2 which is 15-n-octyl-7,15-diazadispiro[5,1,5,3]hexadecane.

15. A composition of matter stabilized against ultraviolet deterioration consisting essentially of a synthetic organic polymer normally subject to ultraviolet deterioration containing from 0.01 to 2% by weight of the polymer of a stabilizing compound according to claim 1.

16. A composition of matter stabilized against ultraviolet deterioration consisting essentially of a synthetic organic polymer normally subject to ultraviolet deterioration containing a stabilizing amount of a hindered phenolic compound and from about 0.01 to 2% by weight of the polymer of a compound according to claim 1.

17. A composition of claim 16 wherein the polymer is a polyolefin.

18. A composition of claim 17 wherein the polyolefin is polypropylene.

19. A composition of claim 17 wherein the hindered phenolic compound is selected from n-octadecyl 3-(3,5-di-t-butyl-4-hydroxyphenyl)propionate, di-n-octadecyl(3,5-di-t-butyl-4-hydroxybenzyl)phosphonate, pentaerythritol-tetrakis[3-(3,5-di-t-butyl-4-hydroxyphenyl)propionate], and tris-(3,5-di-t-butyl-4-hydroxybenzyl)isocyanurate.

20. A composition of claim 17 wherein the antixodiant is di-n-octadecyl(3,5-di-t-butyl-4-hydroxybenzyl)-phosphonate.

21. A composition of claim 17 wherein the substituted piperazine stabilizing compound is 15,15'-dodecamethylene bis(7,15-diazadispiro[5.1.5.3]hexadecane).

22. A composition of claim 17 wherein the substituted piperazine stabilizing compound is 15,15'-octamethylene bis(7,15-diazadispiro[5.1.5.3]hexadecane).

23. A composition of claim 17 wherein the substituted piperazine stabilizing compound is 15,15'-tetramethylene bis(7,15-diazadispiro[5.1.5.3]hexadecane).

* * * * *